(12) United States Patent
Kitamura et al.

(10) Patent No.: US 11,109,877 B2
(45) Date of Patent: Sep. 7, 2021

(54) TREATMENT INSTRUMENT THAT INCLUDES AN OPERATION DIAL

(71) Applicant: OLYMPUS CORPORATION, Hachioji (JP)

(72) Inventors: Ojiro Kitamura, Hachioji (JP); Reisuke Osada, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 265 days.

(21) Appl. No.: 16/448,500

(22) Filed: Jun. 21, 2019

(65) Prior Publication Data
US 2019/0307475 A1    Oct. 10, 2019

Related U.S. Application Data

(63) Continuation of application No. PCT/JP2016/088060, filed on Dec. 21, 2016.

(51) Int. Cl.
*A61B 17/29* (2006.01)
*A61B 17/00* (2006.01)

(52) U.S. Cl.
CPC .... *A61B 17/29* (2013.01); *A61B 2017/00389* (2013.01); *A61B 2017/2902* (2013.01); *A61B 2017/2912* (2013.01); *A61B 2017/2932* (2013.01)

(58) Field of Classification Search
CPC .......... A61B 17/29; A61B 2017/00389; A61B 2017/2902; A61B 2017/2912; A61B 2017/2932; A61B 2017/00367; A61B 2017/00424; A61B 2017/2927

See application file for complete search history.

(56) References Cited

U.S. PATENT DOCUMENTS

| 8,292,889 | B2 | 10/2012 | Cunningham et al. |
| 9,089,321 | B2 | 7/2015 | Snyder et al. |
| 9,113,902 | B2 | 8/2015 | Cunningham et al. |
| 9,265,486 | B2 | 2/2016 | Hughett, Sr. et al. |
| 9,550,041 | B2 | 1/2017 | Bedell |
| 2011/0213362 | A1 | 9/2011 | Cunningham et al. |

(Continued)

FOREIGN PATENT DOCUMENTS

JP    2014-529429 A    11/2014

OTHER PUBLICATIONS

Jun. 25, 2019 Translation of International Preliminary Report on Patentability issued in International Patent Application No. PCT/JP2016/088060.

(Continued)

*Primary Examiner* — Tan-Uyen T Ho
*Assistant Examiner* — Arwa Mostafa
(74) *Attorney, Agent, or Firm* — Oliff PLC

(57) ABSTRACT

A treatment instrument includes a sheath having a longitudinal axis, an end effector provided on one end of the sheath, a housing to which the other end of the sheath is connected, and an operation dial provided to be rotatable relative to the housing around a first rotational axis. The operation dial includes a first outer peripheral surface provided around the first rotational axis, and a second outer peripheral surface spaced apart from the first outer peripheral surface in a direction along the first rotational axis and provided around the first rotational axis.

16 Claims, 8 Drawing Sheets

(56) References Cited

U.S. PATENT DOCUMENTS

| | | |
|---|---|---|
| 2012/0130420 A1* | 5/2012 | Nicholas .......... A61B 17/07207 |
| | | 606/205 |
| 2012/0203142 A1 | 8/2012 | Bedell |
| 2013/0041403 A1 | 2/2013 | Cunningham et al. |
| 2013/0131649 A1 | 5/2013 | Hughett, Sr. et al. |
| 2013/0274797 A1 | 10/2013 | Nicholas et al. |
| 2014/0107673 A1 | 4/2014 | Snyder et al. |
| 2016/0000426 A1 | 1/2016 | Snyder et al. |
| 2016/0113651 A1 | 4/2016 | Privitera et al. |
| 2016/0113656 A1 | 4/2016 | Privitera et al. |

OTHER PUBLICATIONS

Mar. 14, 2017 International Search Report issued in International Patent Application No. PCT/JP2016/088060.

* cited by examiner

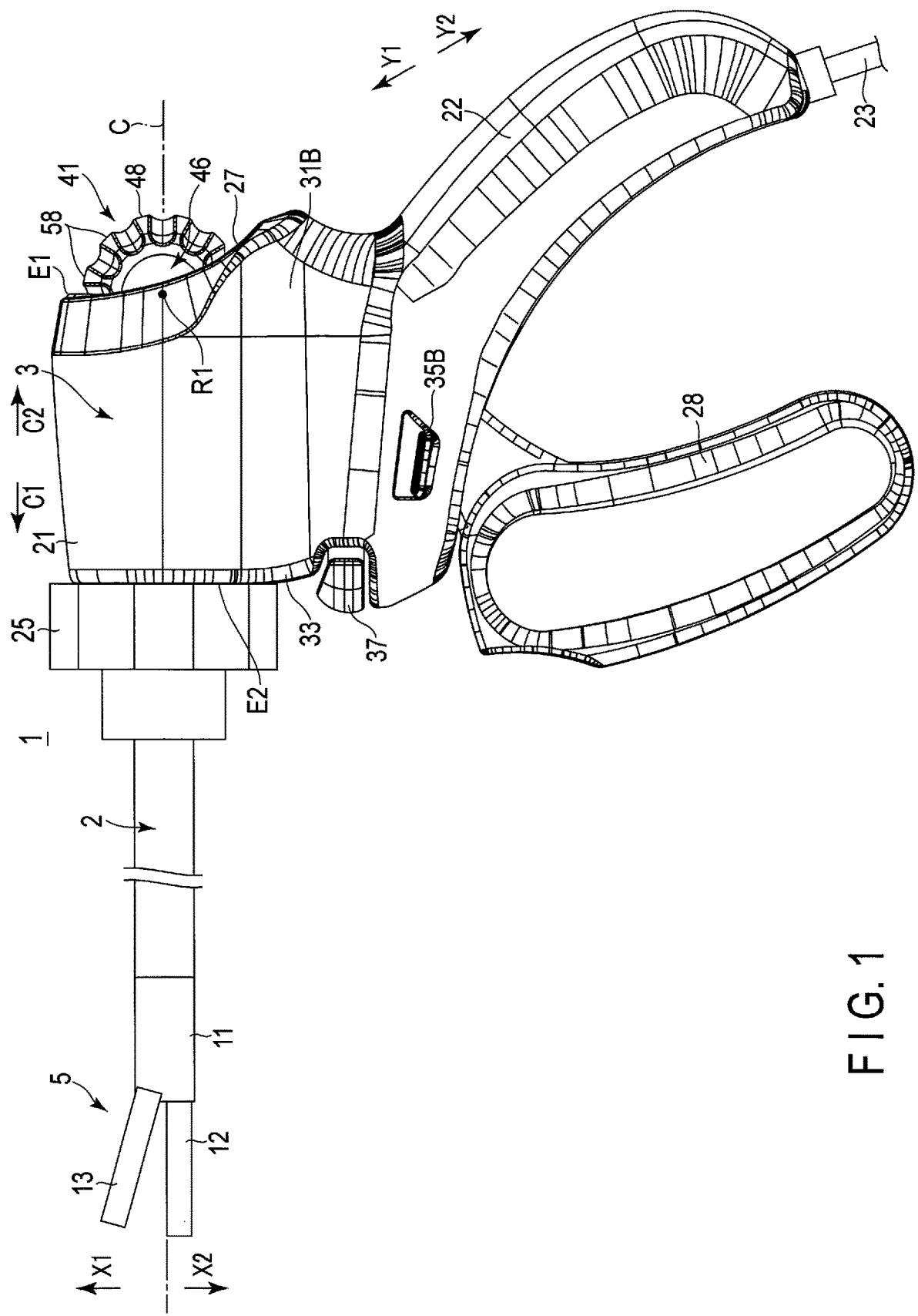
F I G. 1

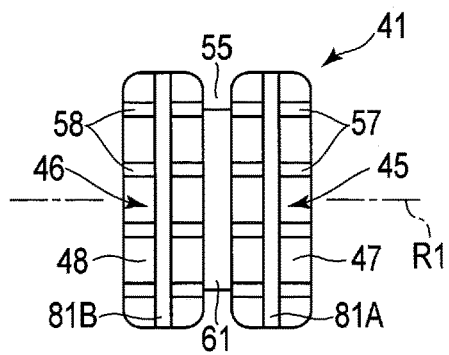
F I G. 9
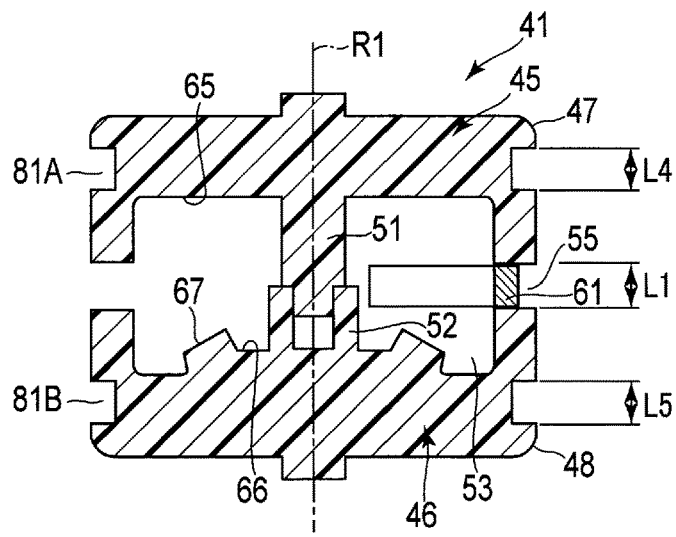
F I G. 10
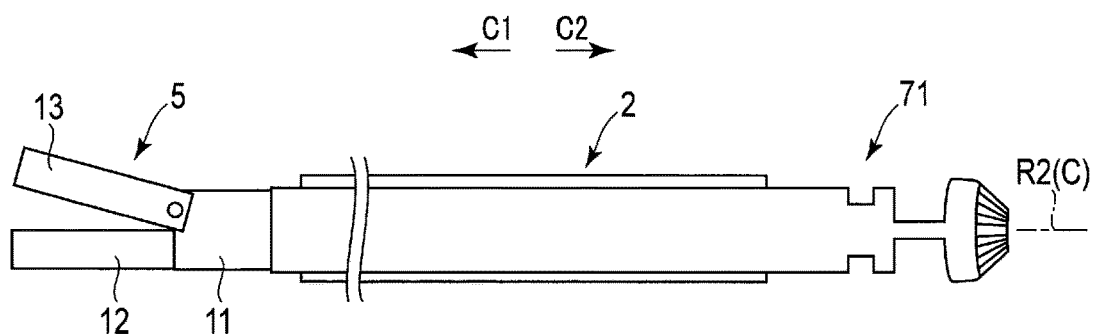
F I G. 11

TREATMENT INSTRUMENT THAT INCLUDES AN OPERATION DIAL

CROSS-REFERENCE TO RELATED APPLICATIONS

This is a Continuation Application of PCT Application No. PCT/JP2016/088060, filed Dec. 21, 2016, the entire contents of which are incorporated herein by reference.

BACKGROUND

Some treatment instruments have housings that can be held. In such a treatment instrument, a shaft is attached to the housing from a distal side, and the housing includes a housing body extending along a longitudinal axis of the shaft. A grip extends from the housing in a direction crossing the longitudinal axis. In addition, an end effector, which treats a treatment target, is provided in a distal portion of the shaft, and the end effector can bend relative to the shaft. An operation dial that bends and moves the end effector is attached to a proximal outer surface of the housing body. The operation dial is rotatable around a rotational axis that extends in a direction crossing the longitudinal axis.

SUMMARY

Exemplary embodiments relate to a treatment instrument including an operation dial for operating an end effector in a treatment instrument.

A treatment instrument can include a sheath having a longitudinal axis; an end effector provided on one end of the sheath; a housing to which the other end of the sheath is connected; an operation dial provided to be rotatable relative to the housing around a first rotational axis, the operation dial including a first outer peripheral surface provided and a second outer peripheral surface spaced apart from the first outer peripheral surface in a direction along the first rotational axis; and a rod configured to transmit driving force which moves the end effector. The operation dial can include a first engagement that is provided inside the operation dial and that is engaged with the rod. The rod can also include a second engagement that extends through a gap between the first outer peripheral surface and the second outer peripheral surface. The second engagement can be engaged with the first engagement inside the operation dial. The rod can move the end effector by rotating around a second rotational axis crossing the first rotational axis in accordance with rotation of the operation dial around the first rotation axis.

The treatment instrument can also have an operation dial that defines an inner cavity, the inner cavity being exposed via the gap between the first outer peripheral surface and the second outer peripheral surface. The treatment instrument can also include a shut-off member configured to cover the gap in a part located on an inner peripheral side of the operation dial with respect to the first outer peripheral surface and the second outer peripheral surface.

The treatment instrument can also include a driving member configured to transmit driving force which moves the end effector; a first operation member provided on the housing. The first operation member can rotate together with the sheath and the end effector relative to the housing around the longitudinal axis. The treatment instrument can also include a second operation member engaged with the driving member such that it rotates relative to the housing around a first rotational axis that intersects the longitudinal axis. The second operation member can rotate together with the sheath and the end effector relative to the housing while the first operation member rotates around the longitudinal axis, and the second operation member can be located on the longitudinal axis.

Advantages will be set forth in the description which follows, and in part will be obvious from the description, or may be learned by practice of the invention. The advantages may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view illustrating a treatment instrument according to an exemplary embodiment as viewed from one side of a width direction of a housing;

FIG. 9 is a schematic view illustrating an operation dial according to an exemplary embodiment;

FIG. 10 is a cross-sectional view schematically illustrating a configuration of the operation dial and a vicinity thereof according to an exemplary embodiment; and FIG. 11 is a schematic view illustrating an example of a transmission configuration of driving force from a rod to an end effector according to an exemplary embodiment.

DETAILED DESCRIPTION

Figure 2:
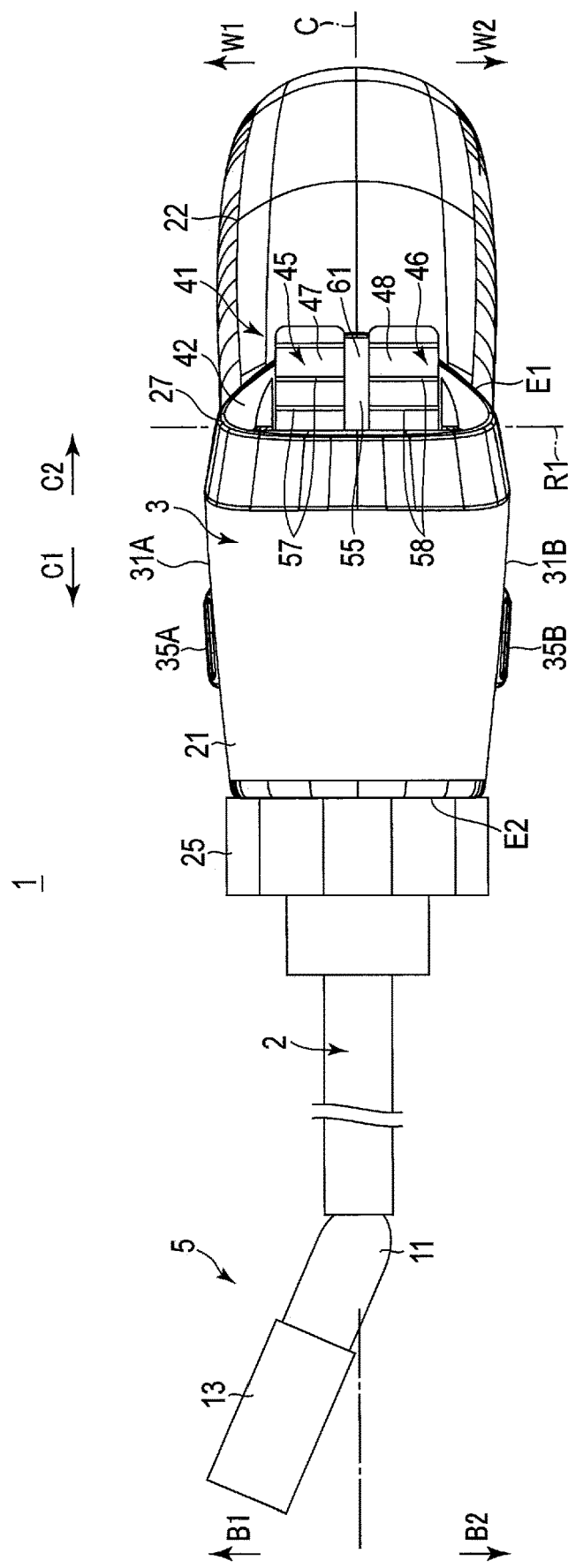
FIG. 2 is a schematic view illustrating the treatment instrument according to an exemplary embodiment as viewed from an opposite side to a side on which a grip is located with respect to a longitudinal axis.

FIG. 1 and FIG. 2 are views illustrating a treatment instrument 1 of the present embodiment. As illustrated in FIG. 1, the treatment instrument 1 includes a shaft (sheath) 2, and the shaft 2 has a longitudinal axis C as a center axis. Here, it is assumed that one side of a direction along the longitudinal axis C is a distal side (arrow C1 side), and an opposite side to the distal side is a proximal side (arrow C2 side). The shaft 2 includes a proximal end and a distal end, and extends from the proximal end to the distal end along the longitudinal axis C.

The treatment instrument 1 includes a housing 3 which can be held. The shaft 2 is attached to the housing 3, and extends from the housing 3 toward the distal side. In addition, a distal portion of the shaft 2 is provided with an end effector 5. In the shaft 2, a side toward the housing 3 is the proximal side, and a side toward the end effector 5 is the distal side. In the present embodiment, the shaft 2 is rotatable relative to the housing 3 around the longitudinal axis C. The end effector 5 is rotatable together with the shaft 2 relative to the housing 3 around the longitudinal axis C. By the rotational movement of the end effector 5 around the longitudinal axis C, the angular position of the end effector 5 around the longitudinal axis C varies. In addition, in the present embodiment, the end effector 5 is bendable relative to the shaft 2 (longitudinal axis C). Bending directions (directions indicated by an arrow B1 and an arrow B2) of the end effector 5 cross (are substantially perpendicular to) the longitudinal axis C.

The end effector 5 includes a relay member 11, a first grasping piece 12 and a second grasping piece 13. The relay member 11 is attached to the distal end of the shaft 2 such that the relay member 11 can bend (can curve) relative to the shaft 2. In addition, in the end effector 5, the pair of grasping pieces 12 and 13 can open and close relative to each other. The opening and closing directions (directions indicated by an arrow X1 and an arrow X2) of the grasping pieces 12 and 13 cross (are substantially perpendicular to) the longitudinal axis C and cross (are substantially perpendicular to) the bending directions of the end effector 5. Here, in one example, one of the grasping pieces 12 and 13 is integral with, or fixed to, the relay member 11, and the other is rotatably attached to the relay member 11. In another example, both the grasping pieces 12 and 13 are rotatably attached to the relay member 11. In still another example, a rod member (not shown) extends from the inside of the relay member 11 toward the distal side, and one of the grasping pieces 12 and 13 is formed by a projecting portion of the rod member from the relay member 11 toward the distal side. In addition, the other of the grasping pieces 12 and 13 is rotatably attached to the relay member 11.

The housing 3 includes a housing body 21 which extends along the longitudinal axis C of the shaft 2. The housing body 21 includes a proximal end E1 and a distal end E2. The housing body 21 extends from the proximal end E1 to the distal end E2 in a state in which the center axis thereof is coaxial or substantially coaxial with the longitudinal axis C. The housing body 21 includes a proximal outer surface 27 which faces the proximal side, and the proximal end E1 of the housing body 21 is formed by the proximal outer surface 27. In addition, the housing 3 includes a grip (stationary handle) 22 which extends from the housing body 21 in a direction crossing the longitudinal axis C. In the present embodiment, the grip 22 is formed integral with the housing body 21. One end of a cable 23 is connected to the housing 3. In the present embodiment, for example, one end of the cable 23 is connected to an end portion of the grip 22 on a far-side from the housing body 21 (longitudinal axis C). The other end of the cable 23 is connected to an energy control device (not shown).

In addition, in the present embodiment, a rotation knob 25 is attached to the distal side of the housing body 21. The shaft 2 is inserted into the inside of the rotation knob 25 and the inside of the housing body 21 from the distal side, and is attached to the housing 3 from the distal side. The rotation knob 25 is fixed to the shaft 2 and is rotatable together with the shaft 2 and end effector 5 relative to the housing 3 around the longitudinal axis C. By rotating the rotation knob 25 around the longitudinal axis C, an operation to rotationally move the shaft 2 and end effector 5 around the longitudinal axis C is input.

Figure 3:
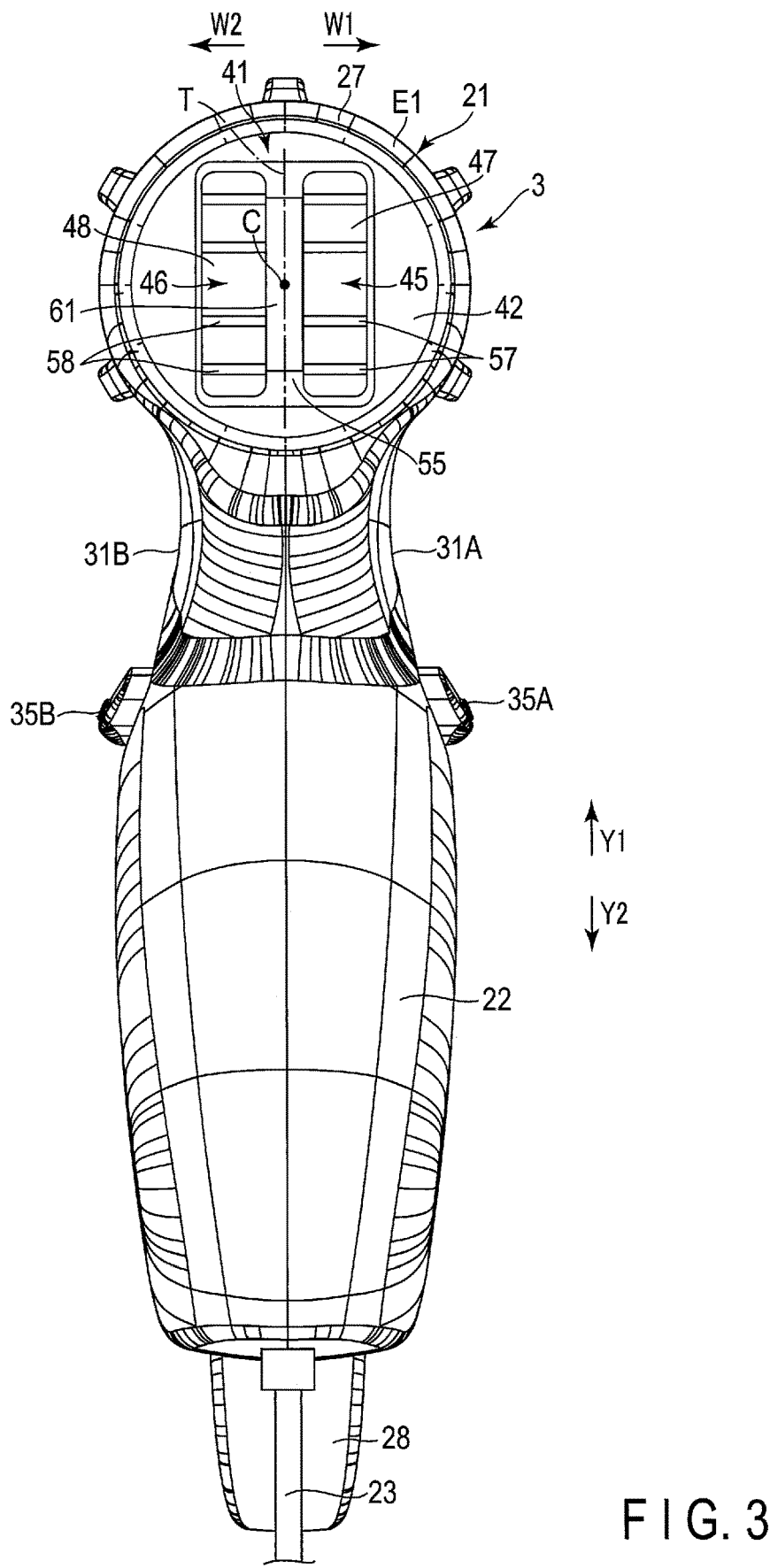
FIG. 3 is a schematic view illustrating a configuration of the housing and a vicinity thereof according to an exemplary embodiment in a state as viewed from a proximal side.

FIG. 3 is a view illustrating a configuration of the housing 3 and a vicinity of the housing 3. Here, it is assumed that a direction crossing (substantially perpendicular to) the longitudinal axis C and crossing (substantially perpendicular to) an extending direction (direction indicated by an arrow Y1 and an arrow Y2) of the grip 22 is a width direction (direction indicated by an arrow W1 and an arrow W2) of the housing 3. FIG. 1 illustrates a state in which the housing 3 is viewed from one side of the width direction, and FIG. 2 illustrates a state in which the housing 3 is viewed from an opposite side to a side on which the grip 22 is located with respect to the longitudinal axis C. In addition, FIG. 3 illustrates a state in which the housing 3 is viewed from the proximal side. As illustrated in FIG. 1 to FIG. 3, the housing 3 includes a lateral outer surface (first lateral outer surface) 31A which faces one side (arrow W1 side) of the width direction, and a lateral outer surface (second lateral outer surface) 31B which faces an opposite side to the lateral outer surface 31A. Further, the housing 3 includes a distal outer surface 33 which extends between the lateral outer surfaces 31A and 31B in the state facing the distal side, and includes the above-described proximal outer surface 27. The distal outer surface 33 forms the distal end E2 of the housing body 21. Besides, the proximal outer surface 27 of the housing body 21 extends between the lateral outer surfaces 31A and 31B.

A handle (movable handle) 28 is rotatably attached to the housing 3. The handle 28, which is an opening and closing operation input section, rotates relative to the housing 3, and thereby the handle 28 opens or closes relative to the grip 22. In the present embodiment, the treatment instrument 1 is a pistol-type treatment instrument, and the handle 28 is located on the side on which the grip 22 is located with respect to the longitudinal axis C, and on the distal side with respect to the grip 22. In addition, a direction of movement in the opening motion and closing motion of the handle 28 relative to the grip 22 is substantially parallel to the longitudinal axis C. In one example, the handle 28 may be provided on the proximal side with respect to the grip 22. Further, in another example, the handle 28 and grip 22 may be provided on opposite sides with respect to the longitudinal axis C, and the direction of movement in the opening motion and closing motion of the handle 28 relative to the grip 22 may be substantially perpendicular to the longitudinal axis C. By the handle 28 opening or closing relative to the grip 22, a movable member (not shown) extending in the inside of the shaft 2 moves relative to the shaft 2 and housing 3 along the longitudinal axis C. Thereby, at least one of the grasping pieces 12 and 13 rotates relative to the relay member 11, and the grasping pieces 12 and 13 open or close relative to each other. By the opening motion or closing motion of the end effector 5 as described above, a treatment target such as a biological tissue can be grasped between the grasping pieces 12 and 13 in the end effector 5.

Besides, in the housing 3, a lateral button 35A is attached to the lateral outer surface 31A, and a lateral button 35B is attached to the lateral outer surface 31B. In addition, a front button 37 is attached to the distal outer surface 33. In the present embodiment, the lateral buttons 35A and 35B and front button 37 are located between the longitudinal axis C and the handle 28 according to the extending direction (direction indicated by the arrow Y1 and arrow Y2) of the grip 22. In each of the lateral buttons 35A and 35B, an operation to actuate the treatment instrument 1 in a first actuation mode is input. On the other hand, in the front button 37, an operation to actuate the treatment instrument 1 in a second actuation mode, which is different from the first actuation mode, is input. In each of the first actuation mode and second actuation mode, for example, like a well-known treatment instrument, electric energy is supplied to the treatment instrument 1 from the above-described energy control device (not shown), and treatment energy for use in a treatment of a treatment target in the end effector 5 is generated. Then, any one of high-frequency current, ultrasonic vibration and heat by a heater is applied as treatment energy to the treatment target grasped between the grasping pieces 12 and 13. In one example, in one of the first actuation mode and second actuation mode, electric energy is supplied to an electric motor (not shown) from the energy control device, and the electric motor is driven. Thereby, a staple is pierced through the treatment target grasped between the grasping pieces 12 and 13.

Figure 4:
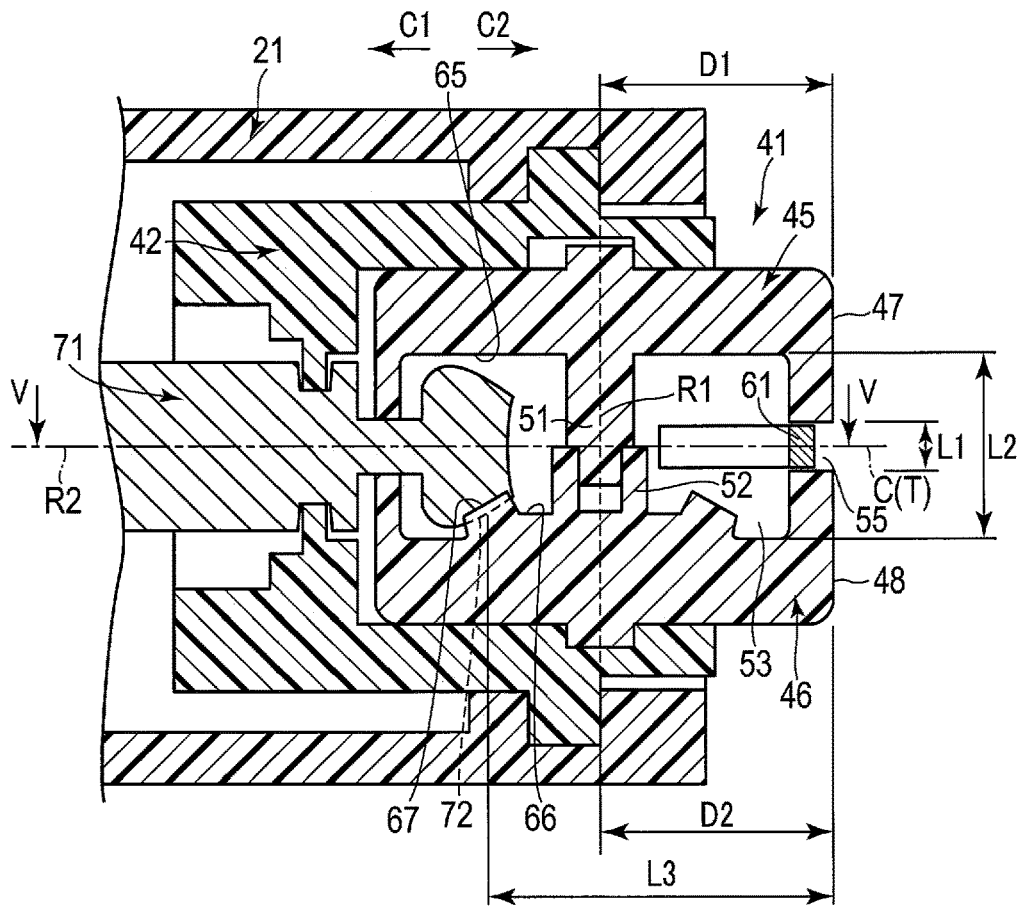
FIG. 4 is a cross-sectional view schematically illustrating a configuration of an operation dial and a vicinity thereof according to an exemplary embodiment.

Furthermore, an operation dial 41 is attached to the proximal outer surface 27 of the housing body 21. In the present embodiment, in the operation dial 41, the above-described operation to bend and move the end effector 5 is input. FIG. 4 is a view illustrating a configuration of the operation dial 41 and a vicinity thereof. As illustrated in FIG. 4, the operation dial 41 is attached to the housing 3 via a block member 42, and the operation dial 41 is supported by the block member 42. In the present embodiment, in the inside of the housing body 21, the block member 42 is coupled to the shaft 2. In addition, by rotating the rotation knob 25 around the longitudinal axis C, rotational driving force around the longitudinal axis C is transmitted from the shaft 2 to the block member 42 and operation dial 41. Thereby, the block member 42 and operation dial 41 rotate together with the shaft 2 and end effector 5 relative to the housing 3 around the longitudinal axis C. In one example, such a configuration may be adopted that even if the rotation knob is rotated around the longitudinal axis C, the rotational driving force is not transmitted to the block member 42 and operation dial 41, and the block member 42 and operation dial 41 do not rotate around the longitudinal axis C.

The operation dial 41 is rotatable relative to the block member 42 around a rotational axis (first rotational axis) R1. In the present embodiment, the rotational axis R1 crosses (is perpendicular to) the direction along the longitudinal axis C. In addition, in the case of the configuration in which the operation dial 41 rotates together with the shaft 2 and end effector 5 around the longitudinal axis C, the rotational axis R1 crosses the direction along the longitudinal axis C even in the state in which the operation dial 41 is located in any angular position around the longitudinal axis C. In the present embodiment, by rotating the operation dial 41 around the rotational axis R1, an operation to bend and move the end effector 5 is input. The operation dial 41 includes a first rotor 45 and a second rotor 46. The rotors 45 and 46 are connected to each other such that the rotors 45 and 46 can rotate together around the rotational axis R1. The first rotor 45 has an outer peripheral surface 47 which extends around the rotational axis R1, and the rotor 46 has an outer peripheral surface 48 which extends around the rotational axis R1. A distance D1 from the rotational axis R1 to the outer peripheral surface 47 and a distance D2 from the rotational axis R1 to the outer peripheral surface 48 are substantially identical. In addition, the first rotor 45 includes a connection shaft 51, and the second rotor 46 includes a connection shaft 52. By the connection shafts 51 and 52 being engaged, the rotors 45 and 46 are connected. In the present embodiment, the connection shafts 51 and 52 extend along the rotational axis R1, with the rotational axis R1 being the center axis thereof.

In addition, in the inside of the operation dial 41, an inner cavity 53 is formed between the rotors 45 and 46 in a direction along the rotational axis R1. The inner cavity 53 neighbors an outer peripheral side of the operation dial 41 with respect to the connection shafts 51 and 52. Further, the outer peripheries of the connection shafts 51 and 52 are surrounded by the inner cavity 53 over the entire circumference around the rotational axis R1. Besides, a gap 55 is formed between the outer peripheral surface 47 of the first rotor 45 and the outer peripheral surface 48 of the second rotor 46 in the direction along the rotational axis R1. In the present embodiment, the gap 55 extends over the entire circumference around the rotational axis R1. The inner cavity 53 is open to the outside of the operation dial 41 via the gap 55. It is preferable that a central position (central plane) T of the operation dial 41 in the direction along the rotational axis R1 passes through the gap 55 and inner cavity 53. It is also preferable that the first rotor 45 and second rotor 46 are mutually symmetric and the outer peripheral surfaces 47 and 48 are mutually symmetric with respect to the central position T which passes through the gap 55. Furthermore, a dimension L1 of the gap 55 in the direction along the rotational axis R1 is less than a dimension L2 of the inner cavity 53 in the direction along the rotational axis R1. It is preferable that the dimension L1 of the gap 55 is 2 mm or more. In addition, the dimension L1 of the gap 55 is such a dimension that the entirety of a finger (e.g. thumb) is not inserted in the gap 55.

Besides, on the proximal outer surface 27 of the housing body 21, a part of the operation dial 41 is exposed to the outside of the housing 3. Thus, the outer peripheral surface 47 of the first rotor 45, the outer peripheral surface 48 of the second rotor 46, and the gap 55 are exposed to the outside of the housing 3 over a partial range around the rotational axis R1. In one example, for instance, the outer peripheral surfaces 47 and 48 and the gap 55 are exposed to the outside of the housing 3 over a range of about 180° around the rotational axis R1. A plurality of projections (first projections) 57, which project toward the outer peripheral side of the operation dial 41, are provided on the outer peripheral surface 47 of the first rotor 45, and a plurality of projections (second projections) 58, which project toward the outer peripheral side of the operation dial 41, are provided on the outer peripheral surface 48 of the second rotor 46. The projections 57 are mutually spaced apart and juxtaposed around the rotational axis R1. It is preferable that the projections 57 are disposed at substantially regular intervals around the rotational axis R1. Similarly, the projections 58 are mutually spaced apart and juxtaposed around the rotational axis R1. In addition, it is preferable that the projections 58 are disposed at substantially regular intervals around the rotational axis R1. Besides, each of the projections 57 is located at substantially the same angular position as the corresponding one of the projections 58 around the rotational axis R1. In the present embodiment, each of the projections 57 extends continuously along the rotational axis R1 between both edges of the outer peripheral surface 47 in the direction along the rotational axis R1. Similarly, each of the projections 58 extends continuously along the rotational axis R1 between both edges of the outer peripheral surface 48 in the direction along the rotational axis R1.

Figure 5:
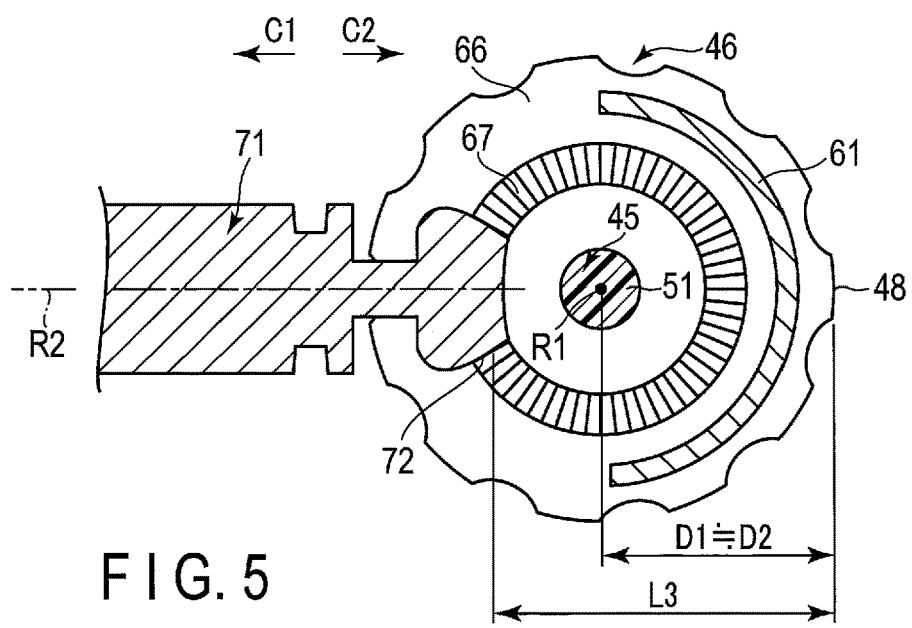
FIG. 5 is a cross-sectional view taken along line V-V in FIG. 4, with the housing and a block member being omitted.

FIG. 5 is a view illustrating a cross section taken along line V-V in FIG. 4, with the housing 3 and block member 42 being omitted. As illustrated in FIG. 4 and FIG. 5, in the present embodiment, a shut-off member 61 is provided in the gap 55. The shut-off member 61 shuts off, in the gap 55, a part of the opening of the inner cavity 53 to the outside of the operation dial 41. The shut-off member 61 is supported by the block member 42, and, even when the operation dial 41 is rotated around the rotational axis R1, the shut-off member 61 does not rotate together with the operation dial 41. The shut-off member 61 extends over a partial range around the rotational axis R1. In addition, the shut-off member 61 extends around the rotational axis R1, at least over a range in which the gap 55 is exposed to the outside of the housing 3. In one example, for instance, the shut-off member 61 extends over a range of at least about 180° around the rotational axis R1. Thus, the exposure of the inner cavity 53 to the outside is prevented by the shut-off member 61. Besides, the shut-off member 61 is located on the inner peripheral side of the operation dial 41, with respect to the outer peripheral surface 47 of the first rotor 45 and the outer peripheral surface 48 of the second rotor 46, and the outer peripheral surface of the shut-off member 61 is recessed to the inner peripheral side of the operation dial 41 with respect to the outer peripheral surfaces 47 and 48. In one example, the shut-off member 61 may not be provided.

The first rotor 45 includes a rotor inner surface (first rotor inner surface) 65 which neighbors the inner cavity 53 and is formed around the rotational axis R1, and the second rotor 46 includes a rotor inner surface (second rotor inner surface) 66 which neighbors the inner cavity 53 and is formed around the rotational axis R1. The rotor inner surface 65 faces the second rotor 46 side, and the rotor inner surface 66 faces the first rotor 45 side. Thus, the rotor inner surfaces 65 and 66 are opposed to each other. In the present embodiment, a gear 67 functioning as a first engagement is formed on the rotor inner surface 66. The gear 67 extends around the rotational axis R1. Although in the present embodiment the gear 67 is formed over the entire circumference around the rotational axis R1, the gear 67 may, in one example, be formed over only a partial range around the rotational axis R1. Further, instead of the gear 67, a gear having the same configuration as the gear 67 may be formed on the rotor inner surface 65 of the first rotor 45. Specifically, it should suffice if the same gear as the gear 67 is provided on a part neighboring the inner cavity 53.

A rod 71 is provided in the inside of the housing body 21. The rod 71 has a rotational axis (second rotational axis) R2 as the center axis thereof, and extends along the rotational axis R2. The rod 71 is supported by the block member 42 and is rotatable relative to the block member 42 around the rotational axis R2. In addition, when the rotation knob 25 is rotated around the longitudinal axis C, the rotational driving force around the longitudinal axis C may be transmitted to the rod 71 or may not be transmitted to the rod 71. Specifically, the rod 71 may rotate together with the shaft 2 and end effector 5 around the longitudinal axis C, or may not follow the rotation of the shaft 2 and end effector 5 around the longitudinal axis C. Further, in the configuration in which the rotational driving force around the longitudinal axis C is transmitted from the rotation knob 25 to the block member 42 and operation dial 41, the rotational driving force may not be transmitted to the rod 71, and the rod 71 may not follow the rotation of the shaft 2 and end effector 5 around the longitudinal axis C. The rotational axis R2 of the rod 71 crosses (is substantially perpendicular to) the direction along the rotational axis R1 of the operation dial 41. In the present embodiment, the rotational axis R2 is substantially parallel to the longitudinal axis C of the shaft 2, and the rotational axis R2 crosses the direction along the rotational axis R1 even in the state in which the operation dial 41 is located in any angular position around the longitudinal axis C. Note that in one example the rotational axis R2 may be coaxial with the longitudinal axis C.

In the inside of the block member 42, the rod 71 is inserted into the inner cavity 53 of the operation dial 41 through the gap 55 from the distal side. Thus, a proximal portion of the rod 71 is disposed in the inner cavity 53. A gear 72 is formed on the proximal portion of the rod 71. The gear 72 is meshed with the gear 67 in the inner cavity 53. Specifically, the gear 72 functions as a second engagement which is engaged with the gear 67 that is the first engagement. In the present embodiment, the gear 72 is formed over the entire circumference around the rotational axis R2. The gears 67 and 72 are bevel gears, for example. Because of the above-described configuration, if the first rotor 45 and second rotor 46 rotate together around the rotational axis R1 by the operation on the operation dial 41, driving force is transmitted to the rod 71 via the gears 67 and 72. Thereby, the rod 71 rotates around the rotational axis R2. By the rotation of the rod 71, driving force is transmitted to the end effector 5, and the end effector 5 is bent and moved as described above.

Figure 6:
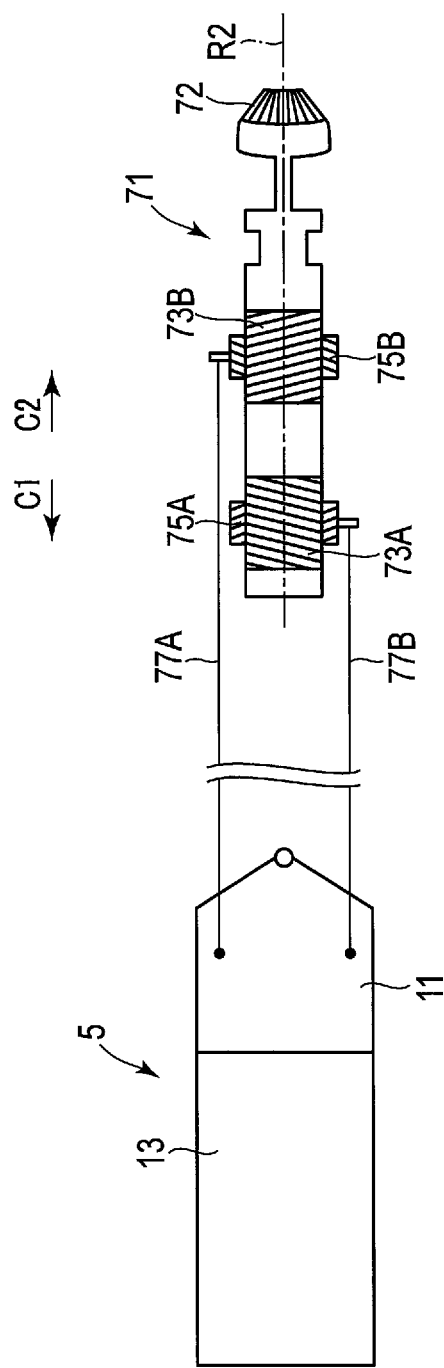
FIG. 6 is a schematic view illustrating an example of a transmission configuration of driving force from a rod to an end effector according to an exemplary embodiment.

Note that an existing configuration is used for the transmission of driving force from the rod 71 to the end effector 5. For instance, in one example illustrated in FIG. 6, a screw portion 73A, and a screw portion 73B having a reverse winding direction to the screw portion 73A, are provided on an outer peripheral surface of the rod 71. The screw portions 73A and 73B are disposed spaced apart from each other in the direction along the rotational axis R2 (the direction along the longitudinal axis C). A nut 75A is threadedly engaged with the screw portion 73A, and one end (proximal end) of a movable member 77A, such as a wire, is connected to the nut 75. In addition, a nut 75B is threadedly engaged with the screw portion 73B, and one end (proximal end) of a movable member 77B, such as a wire, is connected to the nut 75A. The other ends (distal ends) of the movable members 77A and 77B are connected to the end effector 5. By adopting the above-described configuration, when the rod 71 rotates around the rotational axis R2, the nuts 75A and 75B move in mutually opposite directions along the rotational axis R2. Specifically, the nuts 75A and 75B move toward each other or move away from each other in the direction along the rotational axis R2. By the movement of the nuts 75A and 75B as described above, the movable members 77A and 77B move in mutually opposite directions along the longitudinal axis C in the inside of the shaft 2, and the end effector 5 bends.

In another example, in the configuration in which the screw portions 73A and 73B and nuts 75A and 75B are provided, the screw portions 73A and 73B may be movable relative to each other along the rotational axis R2. In this case, one end of the movable member 77A is connected to the screw portion 73A, and one end of the movable member 77B is connected to the screw portion 73B. In the present example, when the rod 71 rotates around the rotational axis R2, the screw portions 73A and 73B move toward mutually opposite sides along the rotational axis R2. Thereby, in the inside of the shaft 2, the movable members 77A and 77B move along the longitudinal axis C, and the end effector 5 bends. In still another example, the rod 71 extends to the distal portion of the shaft 2 along the longitudinal axis C. In addition, the same configuration as the above-described screw portions 73A and 73B, nuts 75A and 75B and movable members 77A and 77B is provided at a distal portion of the rod 71, i.e. in the inside of the distal portion of the shaft 2.

Next, the function and advantageous effects of the treatment instrument 1 of the present embodiment will be described. When treating a treatment target such as a biological tissue by using the treatment instrument 1, a surgeon (user) holds the housing 3 by one hand (left hand or right hand), and inserts the end effector 5 into a body cavity such as an abdominal cavity. Then, the surgeon adjusts the position and attitude of the end effector 5 in the body cavity, by rotating and moving the shaft 2 and end effector 5 around the longitudinal axis C by rotating the rotation knob 25, or by bending the end effector 5 relative to the shaft 2 by operating the operation dial 41. After adjusting the position and attitude of the end effector 5 in the state in which the treatment target is disposed between the grasping pieces 12 and 13, the handle 28 is closed relative to the grip 22. Thereby, the grasping pieces 12 and 13 are closed relative to each other, and the treatment target is grasped between the grasping pieces 12 and 13. In the state in which the treatment target is grasped, the surgeon inputs an operation by the lateral button (35A or 35B), or inputs an operation by the front button 37. Thereby, the treatment instrument 1 is actuated in the first actuation mode or second actuation mode, and treatment energy (high-frequency current or the like) is applied to the treatment target grasped as described above, or a staple is pierced through the treatment target.

In the state in which the housing 3 is held by one hand (right hand or left hand), the palm abuts on the grip 22 from the proximal side. Further, at least one finger of the index finger, middle finger, ring finger and little finger is hooked on the handle 28. In addition, by the finger hooked on the handle 28, operation force which opens or closes the handle 28 relative to the grip 22 is applied. In the state in which an operation is not performed by the operation dial 41, the grip 22 is clamped between the palm and thumb in the width direction of the housing 3. At this time, the thumb extends over one of the lateral outer surfaces 31A and 31B. In addition, the index finger, middle finger, ring finger and little finger extend over the other of the lateral outer surfaces 31A and 31B. For example, when the housing 3 is held by the right hand and no operation is performed by the operation dial 41, the thumb extends over the lateral outer surface 31B, and the index finger, middle finger, ring finger and little finger extend over the lateral outer surface 31A. On the other hand, when the housing 3 is held by the left hand and no operation is performed by the operation dial 41, the thumb extends over the lateral outer surface 31A, and the index finger, middle finger, ring finger and little finger extend over the lateral outer surface 31B.

In the state in which the housing 3 is held by one hand, as described above, the operation for rotating the rotation knob 25 is performed by the index finger or middle finger. The operation on the front button 37 is also performed by the index finger or middle finger. Besides, the operation on the lateral button 35A, 35B is performed by the thumb. Here, for example, when the housing 3 is held by the right hand and the thumb extends over the lateral outer surface 31B, the operation is performed on the lateral button 35B. On the other hand, when the housing 3 is held by the left hand and the thumb extends over the lateral outer surface 31A, the operation is performed on the lateral button 35A.

In the state in which the housing 3 is held by one hand, as described above, the operation on the operation dial 41, which is disposed on the proximal outer surface 27 of the housing body 21, is performed by the thumb. At this time, a fingertip-side part of the thumb is abutted on the operation dial 41, and the operation dial 41 is rotated around the rotation axis R1. In the operation on the operation dial 41, the thumb is abutted on both the outer peripheral surface 47 of the first rotor 45 and the outer peripheral surface 48 of the second rotor 46. At this time, a part of the thumb between an abutment part of the thumb on the first rotor 45 and an abutment part of the thumb on the second rotor 46 is hooked on the rotors 45 and 46 in the gap 55. By the part of the thumb being hooked in the gap 55, the thumb does not easily slip off the operation dial 41, and the surgeon can easily perform the operation on the operation dial 41. Moreover, the fingertip-side part of the thumb abuts on the operation dial 41 on both sides of the hooked part in the gap 55 in the direction along the rotational axis R1. Therefore, the area of contact of the thumb with the operation dial 41 increases, and the operability on the operation dial 41 is enhanced.

In addition, in the present embodiment, the projections 57 are provided on the outer peripheral surface 47 of the first rotor 45, and the projections 58 are provided on the outer peripheral surface 48 of the second rotor 46. Thus, the fingertip-side part of the thumb abuts on the projections 57 and 58, which project to the outer peripheral side of the operation dial 41, on both sides of the hooked part in the gap 55 in the direction along the rotational axis R1. Thereby, the surgeon can more easily perform the operation on the operation dial 41. Besides, by setting the dimension L1 of the gap 55 in the direction along the rotational axis R1 to 2 mm or more, a part of the thumb is properly hooked on the rotors 45 and 46 in the gap 55. Further, by setting the dimension L1 of the gap 55 to such a dimension that the entirety of the finger (e.g. thumb) is not inserted in the gap 55, the thumb is prevented from being inserted into the inner cavity 53. Even when the shut-off member 61 is provided, the entirety of the finger (e.g. thumb) is not inserted in the gap 55 by properly setting the dimension L1 of the gap 55 in the direction along the rotational axis R1, and therefore the contact of the thumb with the shut-off member 61 is prevented. Since the contact of the thumb with the shut-off member 61 that does not rotate together with the operation dial 41 is prevented, the surgeon can more easily perform the operation on the operation dial 41.

Figure 7:
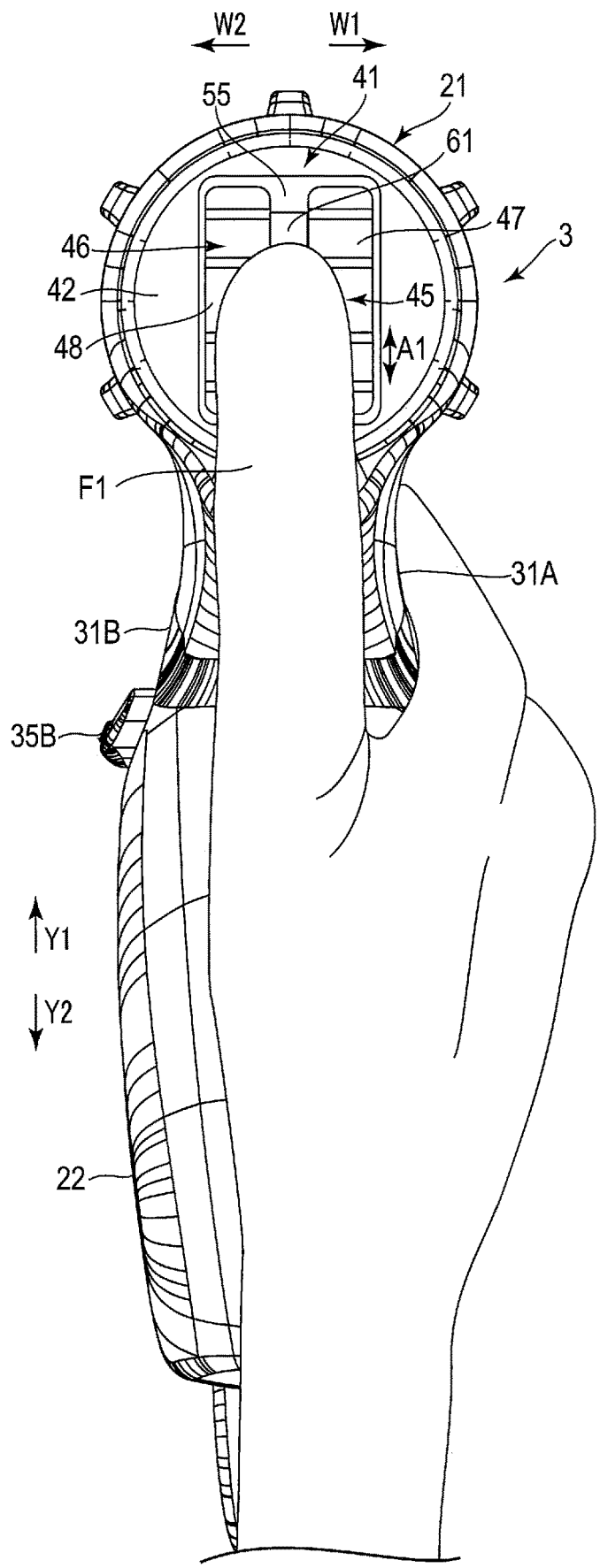
FIG. 7 is a schematic view illustrating a state in which an operation is performed on the operation dial by a thumb in the treatment instrument according to an exemplary embodiment.
Figure 8:
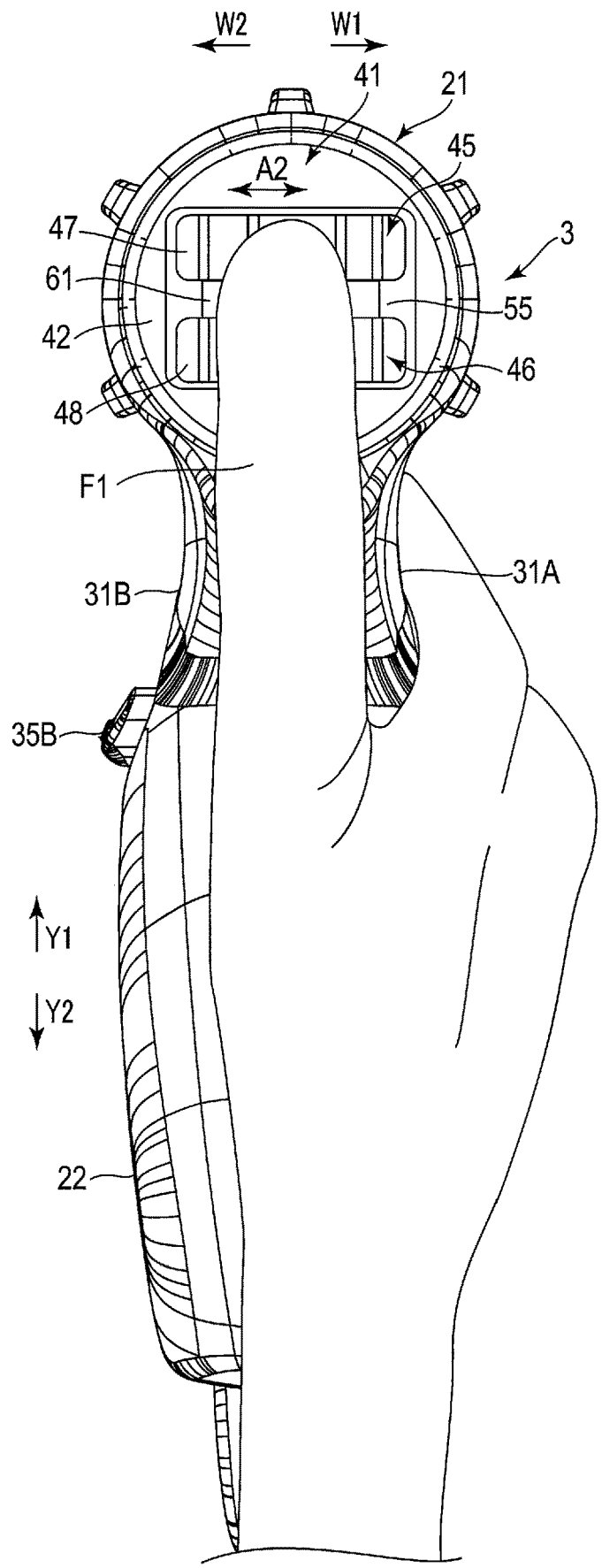
FIG. 8 is a schematic view illustrating a state in which an operation is performed on the operation dial, whose angular position around the longitudinal axis is different than shown in FIG. 7, by the thumb in the treatment instrument according to an exemplary embodiment.

FIG. 7 and FIG. 8 illustrate states in which an operation on the operation dial 41 is performed by a thumb F1. In FIG. 7 and FIG. 8, the angular positions of the operation dial 41 around the longitudinal axis C are different. Specifically, the state of FIG. 7 transitions to the state of FIG. 8 by rotating the rotation knob 25 around the longitudinal axis C and rotating the operation dial 41 and block member 42 together with the shaft 2 around the longitudinal axis C. When the operation is performed, as described above, by the operation dial 41 provided on the proximal outer surface 27 of the housing body 21, the thumb F1 is easily moved substantially in parallel to the extending direction of the handle 28. Accordingly, in the state of FIG. 7, the thumb F1 is easily moved as indicated by an arrow A1 and the operation dial 41 is easily rotated by the thumb F1.

On the other hand, when the operation is performed by the operation dial 41, as described above, the thumb F1 is not easily moved substantially in parallel to the width direction of the housing 3. Accordingly, in the state of FIG. 8, the thumb F1 is not easily moved as indicated by an arrow A2. However, in the present embodiment, a part of the thumb F1 is hooked on the rotors 45 and 46 in the gap 55, and abuts on the operation dial 41 on both sides of the hooked part in the gap 55 in the direction along the rotation axis R1. Thus, in the operation on the operation dial 41, for example, even when it is necessary to move the thumb F1 in a direction in which the movement of the thumb F1 is difficult, such as in the width direction of the housing 3, the operability is ensured and the operation is easily and properly performed by the operation dial 41. Therefore, in the present embodiment, the operability on the operation dial 41 is ensured even in the state in which the operation dial is located in any angular position around the longitudinal axis C.

Additionally, in the present embodiment, the gap 55 is provided over the entire circumference around the rotational axis R1. Thus, the gear (second engagement) 72 of the rod 71 can be inserted into the inner cavity 53 from the gap 55. Further, the gear (first engagement) 67 is provided on the rotor inner surface 65 of the first rotor 45 or the rotor inner surface 66 of the second rotor 46, and the gear 72 of the rod 71 can be engaged with the gear 67. By the engagement between the gear 72 of the rod 71 and the gear 67 of the operation dial 41, the driving force is directly transmitted from the operation dial 41 to the rod 71. Thereby, the loss of driving force from the operation dial 41 to the rod 71 is reduced. Moreover, since the loss of driving force from the operation dial 41 to the rod 71 is reduced, the amount of operation force in the operation on the operation dial 41 can be decreased.

In the meantime, when the gap (55) is not provided, it is necessary to provide a rotary body configured to rotate around a rotational axis that is substantially parallel to the rotational axis (R1) of the operation dial (41) and is located on the distal side with respect to the rotational axis (R1), and in is necessary to transmit driving force from the operation dial (41) to the rod (71) via the rotary body. In this case, in addition to an increase of the above-described loss of driving force, an engaging portion between the rod (71) and the rotary body is provided on the distal side with respect to the distal end of the operation dial (41). Thus, the dimension in the direction along the longitudinal axis (C) from the proximal end of the operation dial (41) to the engaging portion between the rod (71) and the rotary body increases, and the size of the structure for transmitting the driving force from the operation dial (41) to the rod (71) increases. On the other hand, in the present embodiment, in the inner cavity 53, the gear (second engagement) 72 of the rod 71 is engaged with the gear (first engagement) 67 of the operation dial 41. Thus, the engaging portion between the rod 71 and the operation dial 41, i.e. the engaging portion between the gears 67 and 72, is provided on the proximal side with respect to the distal end of the operation dial 41. By virtue of this configuration, a dimension L3 in the direction along the longitudinal axis C from the proximal end of the operation dial 41 to the engaging portion between the rod 71 and operation dial 41 decreases. Thereby, the reduction in size of the structure for transmitting the driving force from the operation dial 41 to the rod can be realized.

As shown in FIG. 9 and FIG. 10, a groove 81A, which is recessed to the inner peripheral side, can be formed on the outer peripheral surface 47 of the first rotor 45, and a groove 81B, which is recessed to the inner peripheral side, can be formed on the outer peripheral surface 48 of the second rotor 46. Each of the grooves 81A and 81B can be formed over the entire circumference around the rotational axis R1. Each of the grooves 81A and 81B can be located at a distance from the gap 55 in the direction along the rotational axis R1. On the outer peripheral surface 47, each of the projections 57 is discontinuous in a part where the groove 81A extends. In addition, on the outer peripheral surface 48, each of the projections 58 can be discontinuous in a part where the groove 81B extends. Note that both grooves 81A and 81B need not be provided, and only one of the grooves 81A and 81B may be provided. When at least one of the grooves 81A and 81B is provided, it should suffice if the dimension L1 of the gap 55 in the direction along the rotational axis R1 is 1.5 mm or more. In this case, too, the dimension L1 of the gap 55 is such a dimension that the entirety of the finger (e.g. thumb) is not inserted in the gap 55. Besides, it is preferable that each of a dimension L4 of the groove 81A in the direction along the rotational axis R1 and a dimension L5 of the groove 81B in the direction along the rotational axis R1 is 1.5 mm or more.

In the operation on the operation dial 41, the thumb is hooked on the rotors 45 and 46 in the gap 55 as described above, and the thumb is hooked on the operation dial 41 in at least one of the grooves 81A and 81B. Thereby, it is possible to further ensure that the thumb does not easily slip off the operation dial 41, and the operability on the operation dial 41 is enhanced.

In addition, in the above-described embodiment, etc., by the driving force being transmitted from the rod 71 to the end effector 5, the end effector 5 is bent and moved. However, the embodiment, etc. are not limited to this. In one modification, by the driving force being transmitted from the rod 71 to the end effector 5, the grasping pieces 12 and 13 open or close relative to each other, and the end effector 5 performs the opening motion or closing motion. In this case, a screw portion (not shown) is formed on the outer peripheral surface of the rod 71, and a nut (not shown) is engaged with the screw portion. Further, one end of a movable member (not shown) is connected to the screw portion or nut, and the other end of the movable member is connected to at least one of the grasping pieces 12 and 13. In the present modification, by the rod 71 being rotated around the rotational axis R2 by the operation on the operation dial 41, the screw portion or nut moves along the rotational axis R2. Thereby, the grasping piece (at least one of 12 and 13), to which the movable member is connected, rotates relative to the shaft 2, and the grasping pieces 12 and 13 open or close relative to each other. In the present modification, as described above, the operation for opening or closing the end effector 5 is input by the operation dial 41. Thus, in the present modification, there is no need to provide the housing 3 with the grip 22, and there is no need to provide the treatment instrument 1 with the handle 28.

Besides, in the above-described embodiment, etc., the rotational movement of the rod 71 around the rotational axis R1 is converted to advancing/retreating movement of the movable member 77A, 77B, etc. along the longitudinal axis C, and the driving force is transmitted to the end effector 5. However, the embodiment, etc. are not limited to this. For example, in a second modification illustrated in FIG. 11, the rotational axis R2 of the rod 71 is substantially coaxial with the longitudinal axis C of the shaft 2. In addition, the rod 71 extends through the inside of the shaft 2, and a distal portion of the rod 71 is coupled to the end effector 5. In the present modification, the end effector 5 is rotatable together with the rod 71 around the longitudinal axis C (rotational axis R2). The shaft 2 is fixed to the housing 3, and the rotation knob 25 or the like is not provided. Thus, the rod 71 is rotatable together with the end effector 5 around the longitudinal axis C, relative to the shaft 2 and housing 3.

The rod 71 can rotate around the rotational axis R2 by the operation on the operation dial 41, and thereby the end effector 5 also rotates together with the rod 71 around the longitudinal axis C (rotational axis R2). Accordingly, the rotational movement of the rod 71, without being converted to advancing/retreating movement or the like, is transmitted from the rod 71 to the end effector 5. Thus, in the present modification, the operation for rotating the end effector 5 relative to the shaft 2 is input by the operation dial 41.

Further, the end effector 5 can be rotatable together with the shaft 2 around the longitudinal axis C, and the rod 71 is coupled to the shaft 2. In addition, the rotational axis R2 of the rod 71 is substantially coaxial with the longitudinal axis C of the shaft 2. In this modification, by the rod 71 rotating around the rotational axis R2 by the operation on the operation dial 41, the shaft 2 and end effector 5 also rotate together with the rod 71 around the longitudinal axis C (rotational axis R2). Accordingly, the rotational movement of the rod 71, without being converted to advancing/retreating movement or the like, is transmitted from the rod 71 to the end effector 5 via the shaft 2. Thus, in the present modification, the operation for rotating the end effector 5 together with the shaft 2 is input by the operation dial 41.

The operation dial (41) can include the first rotor (45) which is rotatable around the rotational axis (R1) passing through the housing (3), and the first rotor (45) includes the outer peripheral surface (47) extending around the rotational axis (R1). The operation dial (41) includes the second rotor (46) which is connected to the first rotor (45) such that the second rotor (46) is rotatable together with the first rotor (45) around the rotational axis (R1), and the second rotor (46) includes the outer peripheral surface (48) extending around the rotational axis (R1). The gap (55) is formed between the outer peripheral surface (47) of the first rotor (45) and the outer peripheral surface (48) of the second rotor (46) in the direction along the rotational axis (R1).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
    a sheath having a longitudinal axis;
    an end effector provided on one end of the sheath;
    a housing to which another end of the sheath is connected;
    an operation dial configured to rotate relative to the housing around a first rotational axis, the operation dial including a first outer peripheral surface and a second outer peripheral surface spaced apart from the first outer peripheral surface in a direction along the first rotational axis such that a gap is provided between the first outer peripheral surface and the second outer peripheral surface and both the first outer peripheral surface and the second outer peripheral surface are provided around the first rotational axis; and
    a rod configured to transmit driving force that moves the end effector,
    wherein:
        the operation dial includes a first engagement which is provided around the first rotational axis in an inside of the operation dial and which is engaged with the rod;
        the rod includes a second engagement extending through the gap between the first outer peripheral surface and the second outer peripheral surface, the second engagement being engaged with the first engagement inside the operation dial; and
        the rod is configured to move the end effector by rotating around a second rotational axis that intersects with the first rotational axis in accordance with a rotation of the operation dial around the first rotational axis.

2. The treatment instrument of claim 1, wherein the gap extends over an entire circumference of the operation dial.

3. The treatment instrument of claim 1, wherein the first outer peripheral surface includes a plurality of first projections which are mutually spaced apart around the first rotational axis,
    each of the first projections projects toward an outer peripheral side and extends along the first rotational axis,
    the second outer peripheral surface includes a plurality of second projections which are mutually spaced apart around the first rotational axis, and
    each of the second projections projects toward an outer peripheral side and extends along the first rotational axis.

4. The treatment instrument of claim 1, wherein the first outer peripheral surface and the second outer peripheral surface are symmetrical with respect to the gap.

5. The treatment instrument of claim 1, wherein the first rotational axis of the operation dial intersects with a direction along the longitudinal axis of the sheath.

6. The treatment instrument of claim 1, wherein the operation dial includes a first rotor including the first outer peripheral surface, and a second rotor including the second outer peripheral surface.

7. A treatment instrument comprising:
    a sheath having a longitudinal axis;
    an end effector provided on one end of the sheath;
    a housing that is connected to another end of the sheath;
    an operation dial configured to rotate relative to the housing around a first rotational axis, the operation dial including a first outer peripheral surface and a second outer peripheral surface spaced apart from the first outer peripheral surface in a direction along the first rotational axis such that a gap is provided between the first outer peripheral surface and the second outer peripheral surface and both the first outer peripheral surface and the second outer peripheral surface are provided around the first rotational axis, the operation dial defining an inner cavity that is exposed via the gap between the first outer peripheral surface and the second outer peripheral surface; and
    a shut-off member configured to cover the gap, the shut-off member being provided on an inner peripheral side of the operation dial with respect to the first outer peripheral surface and the second outer peripheral surface.

8. The treatment instrument of claim 7, wherein the gap extends over an entire circumference of the operation dial.

9. The treatment instrument of claim 7, wherein the first outer peripheral surface includes a plurality of first projections which are mutually spaced apart around the first rotational axis,
    each of the first projections projects toward an outer peripheral side and extends along the first rotational axis,
    the second outer peripheral surface includes a plurality of second projections which are mutually spaced apart around the first rotational axis, and
    each of the second projections projects toward an outer peripheral side and extends along the first rotational axis.

10. The treatment instrument of claim 7, wherein the first outer peripheral surface and the second outer peripheral surface are symmetrical with respect to the gap.

11. The treatment instrument of claim 7, wherein the first rotational axis of the operation dial intersects with a direction along the longitudinal axis of the sheath.

12. The treatment instrument of claim 7, wherein the operation dial includes a first rotor including the first outer peripheral surface, and a second rotor including the second outer peripheral surface.

13. The treatment instrument of claim 7, wherein the shut-off member is supported by the housing and does not rotate in accordance with the rotation of the operation dial around the first rotational axis.

14. A treatment instrument comprising:

a sheath having a longitudinal axis;

an end effector provided on one end of the sheath;

a housing that is connected to another end of the sheath;

a driving member configured to transmit driving force that moves the end effector;

a first operation member provided on the housing and configured to rotate together with the sheath and the end effector relative to the housing around the longitudinal axis; and a second operation member engaged with the driving member and configured to rotate relative to the housing around a first rotational axis that intersects with the longitudinal axis, wherein:

the second operation member is configured to rotate together with the sheath and the end effector relative to the housing while the first operation member rotates around the longitudinal axis, and the second operation member is located on the longitudinal axis.

15. The treatment instrument of claim 14, wherein the second operation member includes a first engagement provided around the first rotational axis in an inside of the second operation member, the first engagement being engaged with the driving member, the driving member includes a second engagement engaged with the first engagement inside the second operation member, and the driving member is configured to move the end effector by rotating around the longitudinal axis in accordance with rotation of the second operation member around the first rotational axis.

16. The treatment instrument of claim 14, wherein the longitudinal axis is an axis that passes through a position where a dimension of the second operation member in a direction along the first rotational axis is halved.

* * * * *